(12) United States Patent
Anderson et al.

(10) Patent No.: US 10,414,579 B2
(45) Date of Patent: Sep. 17, 2019

(54) VENTING SYRINGE

(71) Applicant: CONSORT MEDICAL PLC, Hemel Hempstead (GB)

(72) Inventors: Ian Anderson, Burwell Cambridgeshire (GB); Rachel Suzanne Koppelman, Cambridge (GB); Alastair McKean Willoughby, Cambridge (GB); Joshua Stroobant, Cambridge (GB)

(73) Assignee: CONSORT MEDICAL PLC, Hemel Hempstead (GB)

( * ) Notice: Subject to any disclaimer, the term of this patent is extended or adjusted under 35 U.S.C. 154(b) by 237 days.

(21) Appl. No.: 14/406,172

(22) PCT Filed: Jun. 7, 2013

(86) PCT No.: PCT/GB2013/051512
§ 371 (c)(1),
(2) Date: Dec. 5, 2014

(87) PCT Pub. No.: WO2013/182861
PCT Pub. Date: Dec. 12, 2013

(65) Prior Publication Data
US 2015/0151044 A1 Jun. 4, 2015

(30) Foreign Application Priority Data
Jun. 7, 2012 (GB) .................................. 1210082.2

(51) Int. Cl.
*A61M 5/178* (2006.01)
*B65D 83/24* (2006.01)
(Continued)

(52) U.S. Cl.
CPC ............. *B65D 83/24* (2013.01); *A61M 5/142* (2013.01); *A61M 5/14526* (2013.01);
(Continued)

(58) Field of Classification Search
CPC ............ A61M 5/2053; A61M 5/14526; A61M 5/155; A61M 2005/14513; A61M 2205/8225; A61M 5/2046
See application file for complete search history.

(56) References Cited

U.S. PATENT DOCUMENTS 2,160,367 A 5/1939 Maxfield
2,680,439 A 6/1954 Sutermeister
(Continued)

FOREIGN PATENT DOCUMENTS

AU 2012100112 A4 3/2012
DE 3827525 A1 2/1990
(Continued)

OTHER PUBLICATIONS

International Search Report for International Application No. PCT/GB2013/051512, dated Oct. 29, 2013.
(Continued)

*Primary Examiner* — William R Carpenter
(74) *Attorney, Agent, or Firm* — Marshall, Gerstein & Borun LLP

(57) ABSTRACT

A syringe propellable by a propellant that boils at a predetermined temperature, the syringe comprising a barrel having an outlet at a front end, a stopper axially moveable in the barrel, and a third chamber for containing propellant. The stopper defines and separates a first chamber and a second chamber, the first chamber being axially forwards of the stopper and being configured for containing a medicament, and the second chamber being axially rearwards of the stopper and being configured to receive propellant for acting on the stopper to move the stopper axially forwardly in the barrel to expel medicament through the outlet upon actuation of the syringe. The syringe is configured such that, in use, upon actuation of the syringe, liquid propellant is released from the third chamber and boils outside of the third
(Continued)

chamber at or above the predetermined temperature to provide an increasing vapor pressure in the second chamber that causes the stopper to move axially forwardly and begin to expel medicament from the first chamber through the outlet. During forward axial movement of the stopper in the barrel, propellant vents away from the second chamber through a vent hole.

7 Claims, 19 Drawing Sheets

(51) Int. Cl.
*B65D 83/48* (2006.01)
*B65B 51/26* (2006.01)
*B65B 51/30* (2006.01)
*B65B 31/04* (2006.01)
*A61M 5/20* (2006.01)
*A61M 5/155* (2006.01)
*A61M 39/22* (2006.01)
*A61M 5/168* (2006.01)
*A61M 5/44* (2006.01)
*A61M 5/145* (2006.01)
*A61M 5/142* (2006.01)
*A61M 39/24* (2006.01)

(52) U.S. Cl.
CPC ........ *A61M 5/155* (2013.01); *A61M 5/16804* (2013.01); *A61M 5/16881* (2013.01); *A61M 5/2053* (2013.01); *A61M 5/44* (2013.01); *A61M 39/22* (2013.01); *B65B 31/045* (2013.01); *B65B 51/26* (2013.01); *B65B 51/30* (2013.01); *B65D 83/48* (2013.01); *A61M 2005/14513* (2013.01); *A61M 2039/2486* (2013.01); *A61M 2207/00* (2013.01); *A61M 2207/10* (2013.01); *F04C 2270/0421* (2013.01); *Y10T 29/49* (2015.01); *Y10T 29/49808* (2015.01)

(56) References Cited

U.S. PATENT DOCUMENTS

| | | | |
|---|---|---|---|
| 3,688,765 A * | 9/1972 | Gasaway | A61M 5/30 124/71 |
| 3,977,401 A | 8/1976 | Pike | |
| 4,031,889 A | 6/1977 | Pike | |
| 4,680,027 A * | 7/1987 | Parsons | A61M 5/34 604/68 |
| 4,769,974 A | 9/1988 | Davis | |
| 5,503,627 A * | 4/1996 | McKinnon | A61M 5/24 604/68 |
| 6,096,002 A * | 8/2000 | Landau | A61M 5/30 604/143 |
| 6,210,359 B1 * | 4/2001 | Patel | A61M 5/30 604/68 |
| 6,264,921 B1 | 7/2001 | Johnson et al. | |
| 2003/0233070 A1 * | 12/2003 | De La Serna | A61M 5/2053 604/141 |
| 2004/0073169 A1 * | 4/2004 | Amisar | A61M 5/155 604/141 |
| 2008/0269689 A1 * | 10/2008 | Edwards | A61M 5/2053 604/189 |
| 2011/0270186 A1 * | 11/2011 | Krumme | A61M 5/14526 604/143 |

FOREIGN PATENT DOCUMENTS

| | | |
|---|---|---|
| EP | 2438945 A1 | 4/2012 |
| GB | 2390355 A | 1/2004 |
| JP | 09-010305 A | 1/1997 |
| JP | 2001-224684 A | 8/2001 |
| JP | 2001-521792 A | 11/2001 |
| WO | WO-89/08469 A1 | 9/1989 |
| WO | WO-9922790 A1 | 5/1999 |
| WO | WO-02/083211 A1 | 10/2002 |
| WO | WO-2004/067067 A1 | 8/2004 |
| WO | WO-2005/075009 A1 | 8/2005 |
| WO | WO-2005/115529 A2 | 12/2005 |
| WO | WO-2006/021839 A1 | 3/2006 |
| WO | WO-2009/086250 A1 | 7/2009 |
| WO | WO-2011/050354 A1 | 4/2011 |
| WO | WO-2011/092536 A1 | 8/2011 |

OTHER PUBLICATIONS

International Preliminary Report on Patentability and Written Opinion of International Searching Authority for Application No. PCT/GB2013/051512, dated Dec. 9, 2014.
Japanese Office Action with English Translation for Application No. 2015-515587, dated Apr. 4, 2017.
Great Britain Examination Report under Section 18(3) for Application No. GB1310221.5, dated Mar. 16, 2018.
Office Action, Chinese patent application No. 201380029751.X, dated Oct. 8, 2015.
Examination Report, European patent application No. 13728809.9, dated Jul. 25, 2016.

* cited by examiner

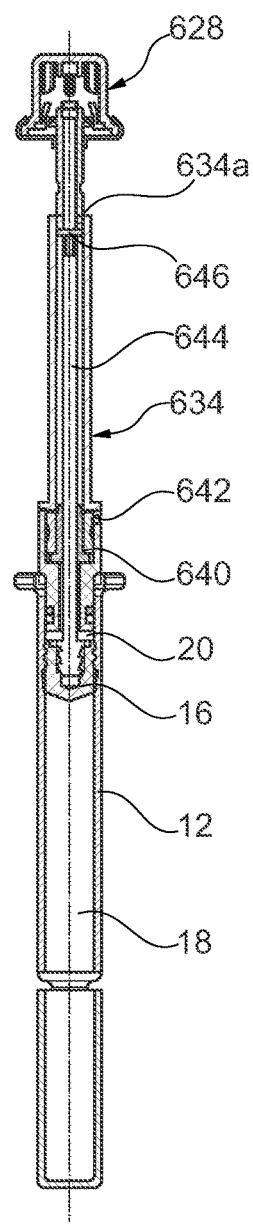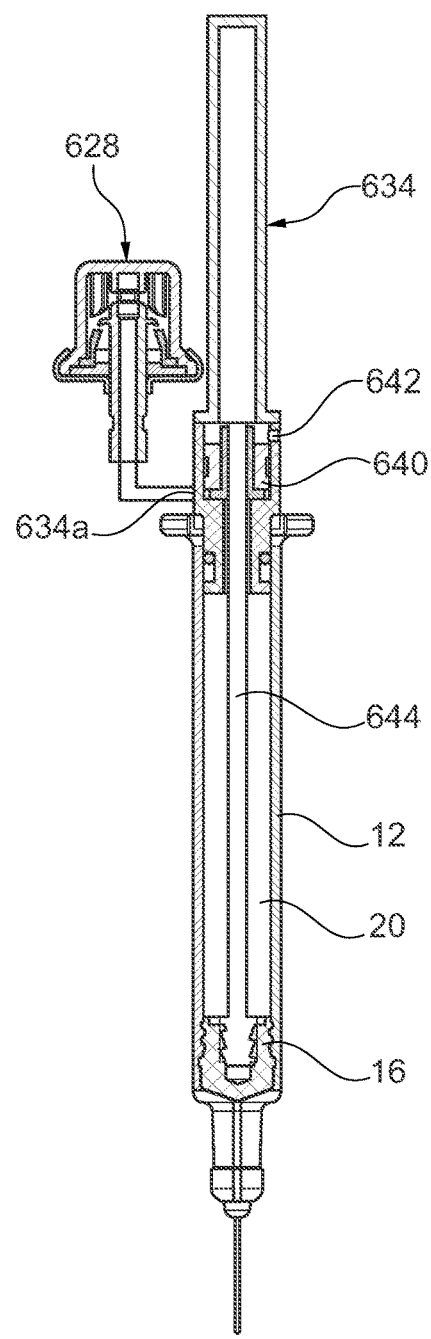
Fig. 3A
Fig. 3B

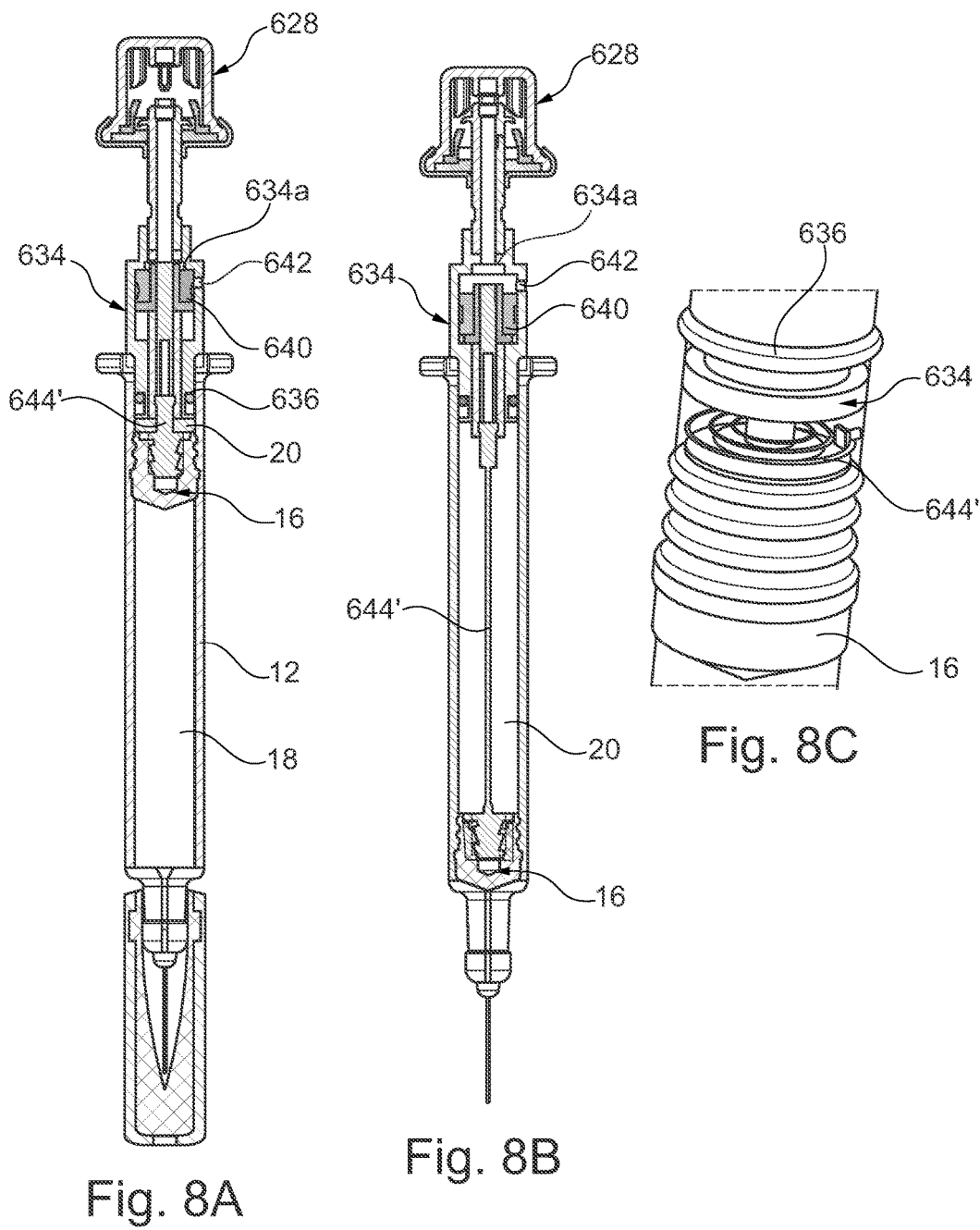

VENTING SYRINGE

CROSS REFERENCE TO RELATED APPLICATIONS

This application is a US national phase under 35 USC § 371 of International Application No. PCT/GB2013/051512, filed Jun. 7, 2013, which claims priority to United Kingdom patent application GB 1210082.2, filed Jun. 7, 2012. Priority application GB 1210082.2 is hereby incorporated by reference.

FIELD OF THE DISCLOSURE

This invention relates to a syringe, and in particular, to a syringe propellable by a propellant that boils at a predetermined temperature, where the syringe is capable of venting propellant therefrom.

BACKGROUND

It is known to power syringes using a gas pressure to move a stopper. In such known devices, a gas spring may provide the gas pressure required to move a stopper in the syringe and deliver a dose of medicament to a patient. When the dose of medicament has been delivered, the syringe still contains the pressurized gas that may present a hazard to the user.

In order to minimize this problem, some gas powered devices include a mechanism for venting the pressurized gas after delivery of medicament is complete.

However, in some prior art devices, tolerance stack up means that the configuration required for venting to occur may not be realized and may result in venting not taking place or taking place less effectively than desired. Additionally, in some prior art devices, tolerance stack up may also be responsible for an incomplete dose of medicament being delivered where there may be variation in the final position of the stopper relative to the forward end of the syringe barrel.

It is an object of at least one embodiment of the present invention to provide an means for venting vapor pressure from a vapor powered syringe that overcomes some of the limitations associated with the prior art. In certain embodiments, it is an object of the present invention to minimize any potential after use risk presented by a syringe powered by a vapor pressure.

BRIEF SUMMARY OF THE DISCLOSURE

In accordance with the present invention there is provided a syringe propellable by a propellant that boils at a predetermined temperature, the syringe comprising:
  a barrel having an outlet at a front end;
  a stopper axially moveable in the barrel; and
  a third chamber for containing propellant;
  wherein the stopper defines and separates a first chamber and a second chamber, the first chamber being axially forwards of the stopper and being configured for containing a medicament, and the second chamber being axially rearwards of the stopper and being configured to receive propellant for acting on the stopper to move the stopper axially forwardly in the barrel to expel medicament through the outlet upon actuation of the syringe;
  the syringe being configured such that, in use, upon actuation of the syringe, liquid propellant is released from the third chamber and boils outside of the third chamber at or above the predetermined temperature to provide an increasing vapor pressure in the second chamber that causes the stopper to move axially forwardly and begin to expel medicament from the first chamber through the outlet;
  wherein during forward axial movement of the stopper in the barrel, propellant vents away from the second chamber through a vent hole.

In one preferable embodiment, the stopper is axially moveable in the barrel between:
  a first position in which the vent hole is not in fluid communication with the first chamber or the second chamber; and
  a second position axially forward of the first position in which the vent hole is in fluid communication with the second chamber thereby permitting venting of propellant from the second chamber.

Further preferably, the stopper is additionally axially moveable in the barrel to a third position that is axially forward of the second position. The third position may be the forwardmost possible position of the stopper in the barrel in which the first chamber has substantially zero volume and substantially all medicament has been expelled from the first chamber. In either case, when in the second position, the syringe preferably contains liquid propeallent. Further preferably, when in the second position, the syringe contains sufficient liquid propellant for the stopper to reach the third position.

In a further or alternatively preferable embodiment, in the first position the stopper blocks fluid communication between the vent hole and the first chamber and between the vent hole and the second chamber, and in the second position the stopper is axially forward of at least part of the vent hole such that the vent hole is in fluid communication with the second chamber.

The stopper may comprise a bung and a piston extending axially rearwardly from the bung, wherein each of the bung and the piston seals to the barrel, the piston being configured to be acted upon by vapor pressure in the second chamber so as to cause the stopper to move axially in the barrel.

Alternatively, the stopper may include a rearwardly axially extending rod that, in the first position, extends through the vent hole and seals to the vent hole so as to block fluid communication between the vent hole and the first chamber and between the vent hole and the second chamber, and, in the second position, the rod does not extend through the vent hole so that the vent hole is in fluid communication with the second chamber. The vent hole may comprise a seal for sealing against the rod.

In one preferable embodiment, the syringe further comprises a blocking member that is moveable between a blocking position in which fluid communication between the vent hole and the second chamber is blocked by the blocking member, and a non-blocking position in which the vent hole is in fluid communication with the second chamber;
  wherein the blocking member is moveable between the blocking position and the non-blocking position by the stopper such that in the first position the blocking member is in the blocking position and in the second position the blocking member is in the non-blocking position.

The stopper may be selectively engageable with the blocking member such that when the stopper is not engaged with the blocking member, the stopper is forwardly axially moveable relative to the blocking member, and when the stopper is engaged with the blocking member forward axial movement of the stopper causes forward axial movement of the blocking member towards the non-blocking position.

The stopper may include a rearwardly axially extending rod extending through blocking member where the rod includes a radial projection at a rear end thereof, wherein the stopper is able to move relative to the blocking member until the projection contacts the blocking member to engage the stopper to the blocking member.

Alternatively, the stopper may include a bung and an extendible member that is connected to the blocking member and the bung, wherein the extendible member is able to extend in axial length and permit forward axial movement of the bung relative to the blocking member until the extendible member reaches a maximum axial extension due to the relative axial distance between the bung and the blocking member causing the stopper to engage with the blocking member.

In one embodiment, the extendible member may be a coil. In an alternative embodiment, the extendible member may be a flexible tether which may comprise string.

In one preferable embodiment, upon actuation of the syringe the vent hole is in fluid communication with the second chamber such that propellant may vent from the second chamber, where the rate of venting through the vent hole is such that the vapor pressure in the second chamber may still rise sufficiently to cause the stopper to move axially forwardly in the barrel.

The stopper may include an occlusion member that, in at least one axial position of the stopper in the barrel, occludes the vent hole so as to limit the rate of venting therethrough without preventing venting entirely.

In one embodiment, the occlusion member may not occlude the vent hole when the stopper is in its forwardmost possible position in the syringe barrel in which the first chamber has substantially zero volume and substantially all medicament has been expelled from the first chamber.

The vent hole may be elongate such that the occlusion member may occlude the vent hole along the elongate length of the vent hole.

The third chamber may initially contain a sufficient volume of propellant to move the stopper to its forwardmost possible position in the barrel in which the first chamber has substantially zero volume and substantially all medicament has been expelled from the first chamber.

In any embodiment, the vent hole may be formed in the barrel. Alternatively, the syringe may further comprise a propellant housing sealed to the barrel, and the vent hole may be formed in the propellant housing.

The propellant may include a hydrofluoroalkane (HFA), which may be HFA 134a.

In some preferable embodiments, the vent hole has an axial length and the axial distance between the stopper in the second position and the stopper in the third position is greater than the axial length of the vent hole. The axial distance between the stopper in the second position and the stopper in the third position may be at least two times greater than the axial length of the vent hole.

In certain embodiments, the propellant may vent away from the second chamber to the outside environment through the vent hole. In alternative embodiments, the propellant may vent away to a further chamber from the second chamber through the vent hole, where the further chamber has a lower pressure than the second chamber.

BRIEF DESCRIPTION OF THE DRAWINGS

Embodiments of the invention are further described hereinafter with reference to the accompanying drawings, in which:

FIG. 3A show a syringe in accordance with an embodiment of the present invention that includes a vent hole;

FIG. 3B shows a syringe in accordance with an alternative embodiment of the present invention that includes a vent hole;

FIGS. 8A and 8B show a syringe in accordance with an alternative embodiment of the present invention that includes a vent hole, where in FIG. 8A the vent hole is closed, and in FIG. 8B the vent hole is open;

FIG. 8C shows a detailed view of part of the syringe of FIGS. 8A and 8B;

DETAILED DESCRIPTION

Figure 6A:
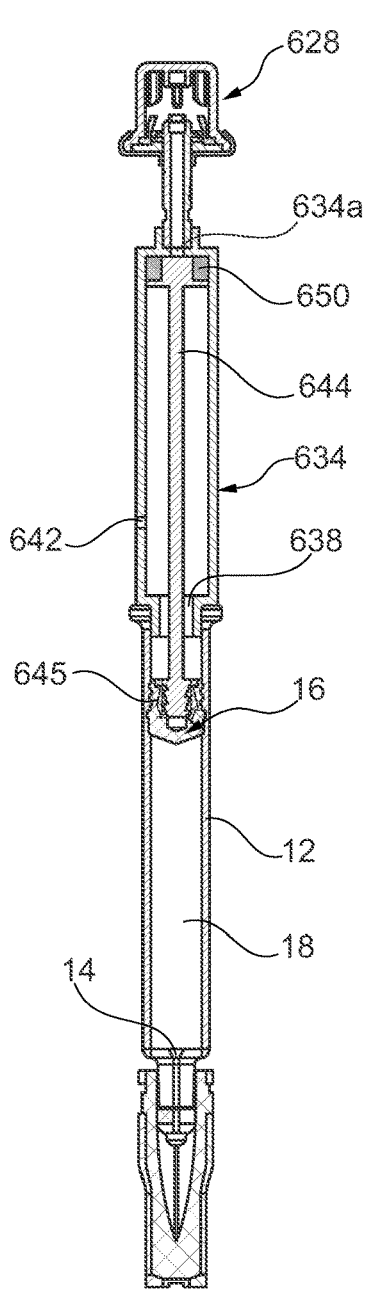
FIGS. 6A and 6B show a syringe in accordance with an alternative embodiment of the present invention that includes a vent hole, where in FIG. 6A the vent hole is closed, and in FIG. 6B the vent hole is open.
Figure 6B:
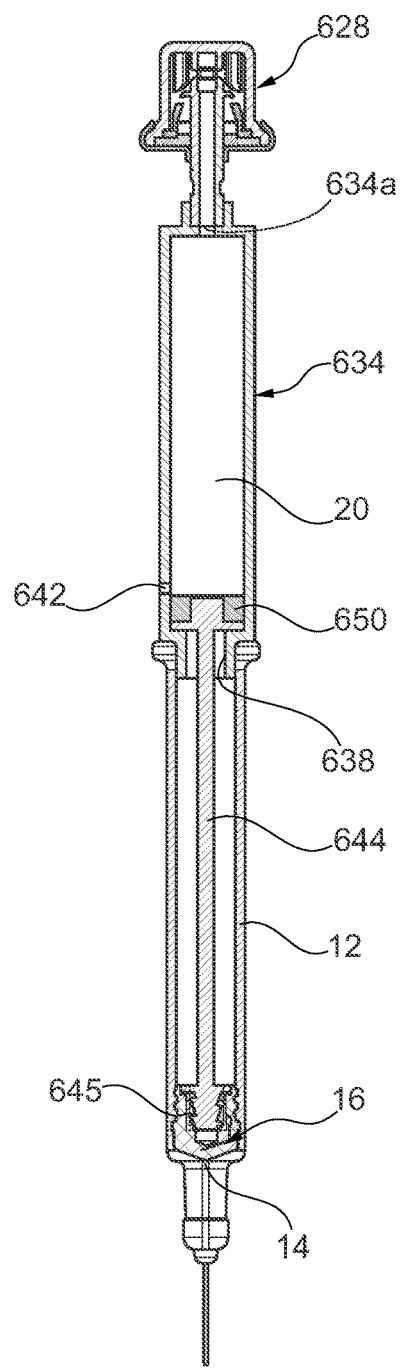

An embodiment of the present invention is shown in FIGS. 6A and 6B which show a syringe comprising a barrel 12 having an outlet 14 at a front end and a stopper 16 disposed in the barrel. In the particular embodiment shown in FIGS. 6A to 6D, the stopper 16 includes a bung 645 at a forward end and a rod 644 extending axially rearwardly from the bung 645 parallel to the length of the syringe barrel 12. The rod 644 extends out of the syringe barrel 12 and into a propellant housing 634 that is disposed at a rear end of the syringe barrel 12 and is sealed thereto. A rear end of the rod 644 is sealed with a piston seal 650 against an inside surface of the propellant housing 634. The propellant housing 634 effectively provides an extension of the syringe barrel 12 and in certain embodiments may not be present if the syringe barrel 12 is sufficiently long in an axial direction. The stopper 16 (taken as a whole, i.e. including the bung 645, rod 644 and piston seal 650) defines and separates a first chamber 18 and a second chamber 20. The first chamber 18 is axially forwards of the stopper 16 and is configured for containing a medicament. The second chamber 20 is axially rearwards of the stopper 16 and is configured to receive propellant for acting on the stopper 16 to move the stopper axially forwardly in the barrel 12 to expel medicament through the outlet 14 upon actuation of the syringe. The syringe includes a third chamber 628 that acts as a propellant source containing a propellant that boils at a predetermined temperature. Suitable propellants are liquefied gases that include hydrofluoroalkanes (HFA), and a particularly suitable propellant is HFA 134a.

In use, upon actuation of the syringe, the third chamber 628 releases liquid propellant that boils outside of the third chamber 628 at or above the predetermined temperature to produce a vapor that is fluidly connected to the second chamber 20. In some embodiments, the liquid propellant may be released directly from the third chamber 628 to the second chamber 20 where it boils to produce the vapor pressure. In alternative embodiments within the scope of the present invention, liquid propellant may be released into a fourth chamber where it may boil and provide a vapor pressure to the second chamber 20. In any embodiment, the propellant must vaporize outside of the third chamber and provide a vapor pressure to the second chamber 20. By ensuring that the third chamber 628 releases liquid propellant that vaporizes at or above the predetermined temperature, a more reliable, predictable and controllable pressure profile results improving the reliability and controllability of the syringe. Additionally, the resulting pressure profile is of such a magnitude that a dose of medicament may be delivered using a relatively small volume of propellant. This is in stark contrast to devices powered by compressed gas where a large volume of compressed gas is required to deliver a dose of medicament (in comparison with a liquefied gas propellant) and provides a very high starting pressure that compensates for the inherent pressure drop of the compressed gas as it expands and causes the stopper to move.

Returning to the present invention, as the vapor pressure in the second chamber 20 rises, the stopper 16 begins to move axially forwardly and begins to expel medicament our of the outlet. In certain embodiments (as with that of FIGS. 6A to 6D), a needle may be attached to the outlet 14 for carrying expelled medicament to an injection site.

In accordance with the present invention, during forward axial movement of the stopper 16 in the barrel 12, propellant vents away from the second chamber 20 through a vent hole. The present invention therefore provides an automatic means for ensuring that the syringe is depressurized after use. This venting may be to the outside environment ("atmosphere") or a further chamber having a lower pressure than the second chamber, and is described in more detail below with reference to several distinct embodiments within the scope of the present invention.

In addition to improving safety, venting during axial movement of the stopper allows the pressure profile within the second chamber to be controlled and manipulated during delivery. The controlled pressure profile may be used to control the rate or force of delivery, or trigger a further action caused by the controlled vapor pressure.

Figure 14A:
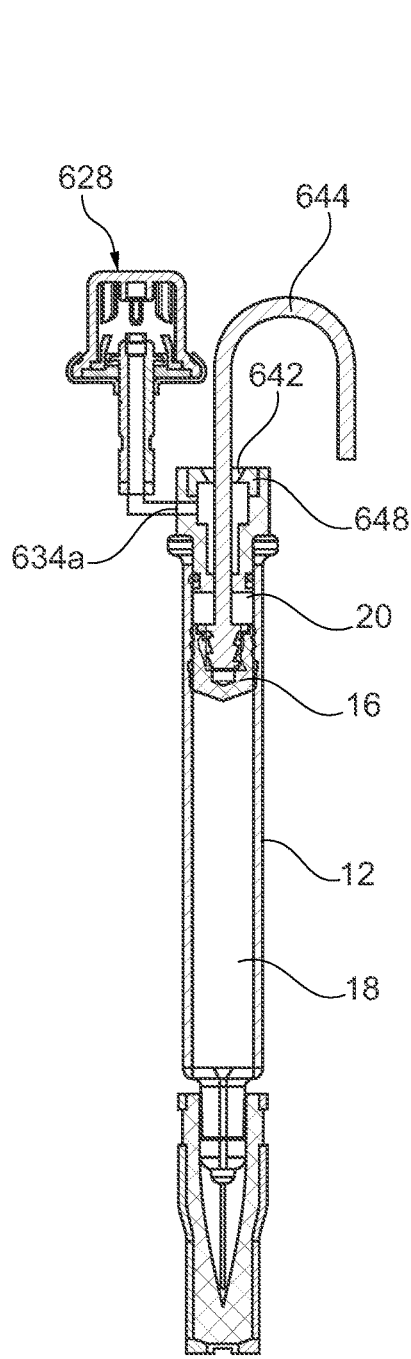
FIGS. 14A and 14B show a syringe in accordance with an alternative embodiment of the present invention that includes a vent hole, where in FIG. 14A the vent hole is closed, and in FIG. 14B the vent hole is open.
Figure 14B:
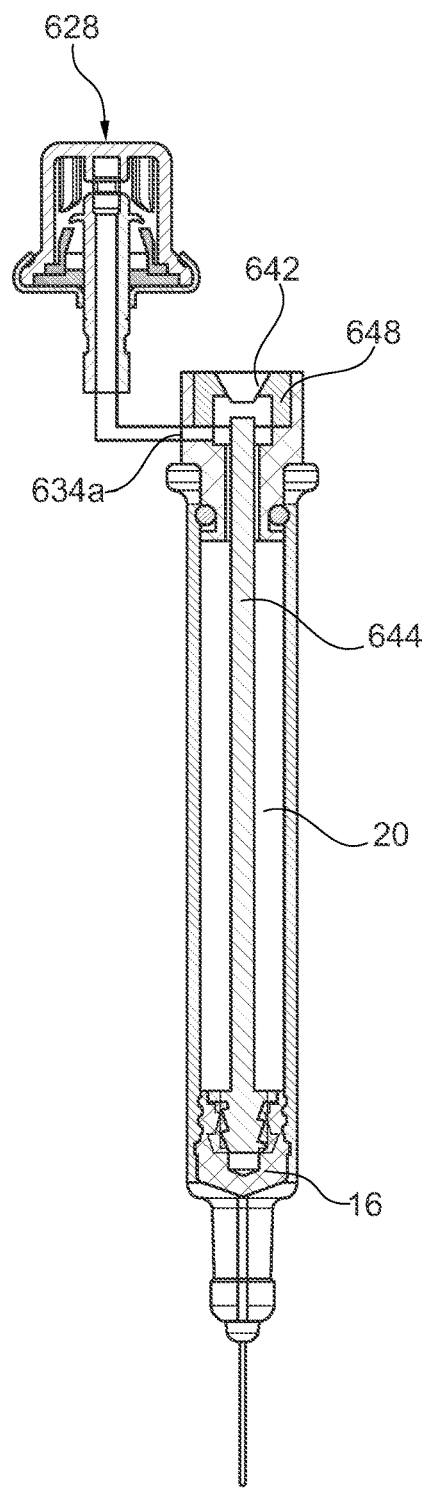
Figure 15:
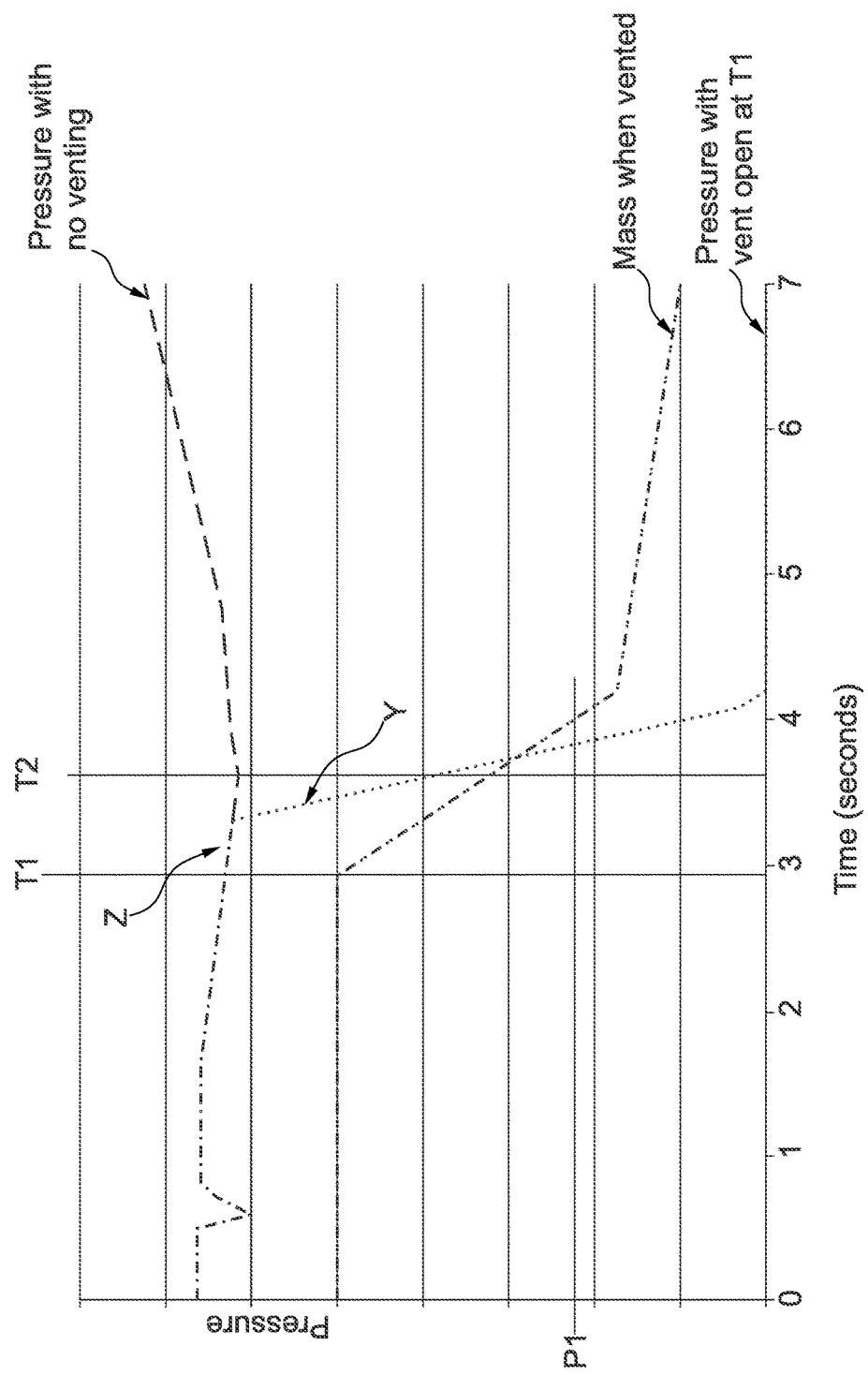
FIG. 15 shows pressure plots of a syringe with venting and without venting, and a plot of the mass of gaseous propellant in the second chamber of the vented syringe, where the propellant is a liquefied gas.
Figure 16:
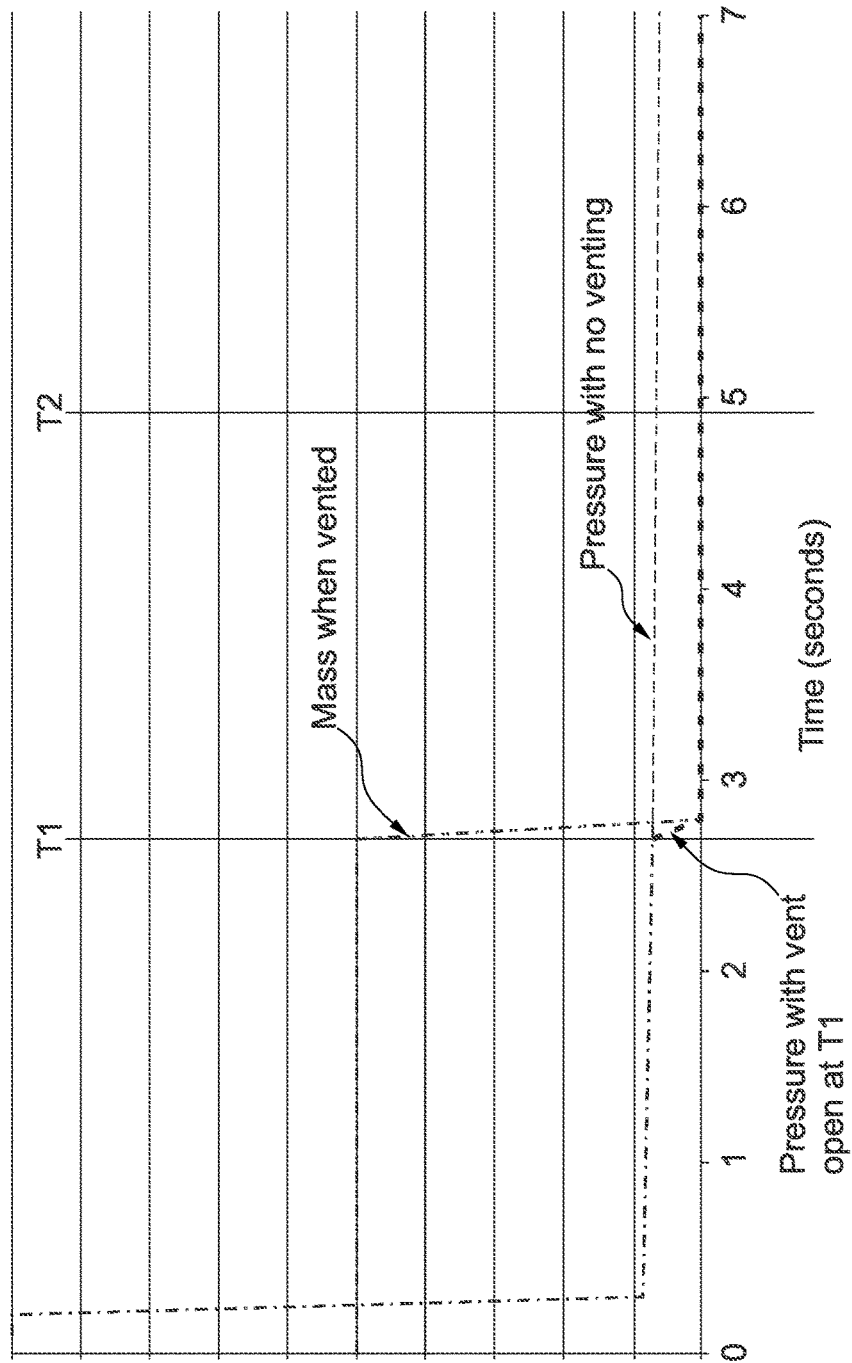
FIG. 16 shows pressure plots of a syringe with venting and without venting, and a plot of the mass of gaseous propellant in the second chamber of the vented syringe, where the propellant is a compressed gas.

Certain advantages of using a liquefied gas as a propellant over a compressed gas are evident by comparing FIGS. 15 and 16. FIG. 15 shows the pressure profiles of two syringe powered by a liquefied gas propellant, where in one syringe a vent hole opens at time T1. In both cases, the delivery is complete at time T2. FIG. 14 additionally shows how the overall mass of vaporized propellant in the second chamber changes over time for the syringe with a vent hole.

For the syringe with no vent hole, the pressure decreases slightly during delivery due to cooling of the propellant as it vaporizes. Then, after delivery is complete (T2), the pressure gradually rises as some of the remaining liquid propellant vaporizes due to heat from its surroundings until equilibrium and a saturated vapor pressure is attained.

For the syringe with a vent hole, when the vent opens at T1 the pressure is initially approximately maintained as liquid propellant continues to vaporize and provide pressure the second chamber. Then prior to the end of delivery, the pressure begins to decrease. This is partly due to the temperature drop arising from an energy drop as the liquid propellant vaporizes and vents through the vent hole. The pressure then falls away to 0 bar relative to atmosphere. Considering the mass of vaporized propellant in the second chamber, FIG. 15 shows that the mass begins decreasing steadily from when the vent hole is opened at T1. The reason that this is a gradual decrease and not a sharp instantaneous drop is that the liquid propellant still remaining in the syringe continues to vaporize and therefore provides new mass of vaporized propellant. After the initial decrease, the rate of decrease slows as a steady state is reached in which the liquid propellant vaporizes but such vaporized propellant merely vents and does not increase the pressure in the second chamber. FIG. 15 also shows the critical pressure threshold P1 above which there is sufficient force to overcome the friction and stiction of the stopper in order to axially move the stopper in the barrel. Pressures below P1 are insufficient for axially moving the stopper in the barrel.

As can be seen from FIG. 15, the pressure of the vented syringe remains notably higher than P1 at T2 therefore providing a device that is able to reliably deliver a complete dose of medicament.

In contrast, FIG. 16 shows the same scenario for a syringe powered by a compressed gas (outside the scope of the present invention). FIG. 16 shows the pressure profile of a syringe powered by a compressed gas where there is no venting, and additionally shows the pressure profile of a syringe powered by a compressed gas where a vent hole opens at time T1. FIG. 16 also shows the corresponding change in mass of gaseous propellant in the second chamber over time. In both vented and non-vented cases, delivery is complete at T2. As shown in FIG. 16, in both the vented and non-vented syringes, the pressure drops rapidly when delivery begins. For the non-vented syringe, a residual pressure remains following the rapid decrease which then slowly decreases until the end of delivery at T2. In contrast, for the vented syringe, the pressure drops rapidly once more when the vent is opened at T1 and decreases to substantially zero. The corresponding plot of mass shows that substantially all of the gaseous mass disappears from the second chamber when the vent hole is opened at T1.

Compressed gas powered devices are therefore not suitable for venting during movement of the stopper in the barrel due the rapid decrease in pressure in the second chamber. This would result in movement of the stopper arresting almost immediately.

In accordance with embodiments of the present invention, venting whilst the stopper is axially moving as opposed to venting when the stopper is stationary permits reliable venting that occurs during delivery and accounts for possible variations in the dimensions of the components of the syringe due to tolerance (so-called tolerance stack up). If, for example, the stopper had to move entirely to the forward end of the syringe barrel before venting occurred, tolerance stack up may mean that due to the relative positions of components key to venting (e.g. the stopper and the vent hole) venting does not take place as effectively as desired or not at all. The present invention may ensure venting occurs in a configuration that is guaranteed to occur irrespective of tolerance stack up, and permit a full dose of medicament to be delivered. Again tolerance stack up in certain prior art syringes may result in an incomplete dose being delivered.

One embodiment of the present invention is shown in FIGS. 1A to 1E. In this embodiment, a propellant housing 634 is sealed by seals 636 to a rear end of the syringe barrel 12. The propellant housing 634 has a vent hole 642 that may be any shape, size or configuration provided that it permits vaporized propellant to pass therethrough. In certain embodiments, the vent hole 642 is preferably small so as to limit the venting rate. Disposed in the syringe barrel 12 is a stopper 16 that includes a rod extending axially rearwardly through the propellant housing 634. The propellant housing 634 has a narrowed forward portion 638, however the narrowed forward portion has a diameter that is larger than the diameter of the rod 644 such that vaporized propellant may pass through the annulus between the rod 644 and the narrowed forward portion 638. Disposed around the rod 644 is an axially moveable seal 640. The axially moveable seal 640 is axially moveable relative to the rod 644 and seals against an inside surface of the propellant housing 634. The axially moveable seal 640 does not seal to the rod 644 entirely (or not at all) and permits the passage of vaporized propellant across the axially moveable seal 640 (i.e. from axially rearward of the axially moveable seal 640 to axially forward of the axially moveable seal 640).

In use, liquid propellant is provided from a propellant source to provide a vapor pressure in the second chamber 20 that extends between the propellant source and the stopper 16. In the configuration shown in FIG. 1A, the axially moveable seal 640 is sealing the vent hole 640 from the second chamber 20 such that propellant cannot escape from the second chamber 20 via the vent hole. In accordance with the present invention, the vapor pressure in the second chamber 20 rises as the liquid propellant boils and the stopper 16 begins to move axially forwardly to begin to expel medicament from the first chamber 18. As the stopper 16 moves axially forwardly, the rod 644 slides axially through the axially moveable seal 640 that remains stationary, sealing the vent hole 640.

Figure 1A:
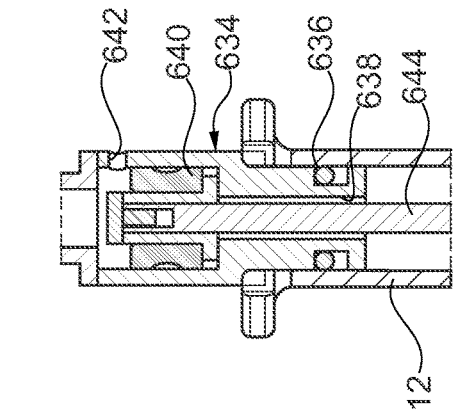
FIG. 1A shows a partial cross section of a syringe in accordance with an embodiment of the present invention that includes a vent hole, where, in FIG. 1A, the vent hole is closed.
Figure 1B:
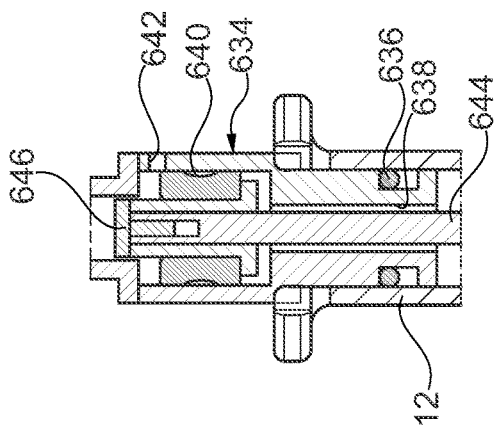
FIG. 1B shows the syringe of FIG. 1A with the vent hole partially open.

As shown in FIG. 1B, a flange 646 projects from a rear end of the rod 644. When the stopper 16 reaches an axial position in the syringe barrel 12 where the flange 646 contacts the axially moveable stopper 640, further axially forwardly movement of the stopper 16 causes the flange 646 to move the axially moveable seal 640 axially forwardly and begin to open the vent hole 642. FIG. 22B shows the vent hole 642 partially opened by the axially forwardly advancing axially moveable seal 640. As the vent hole 642 opens, propellant in the second chamber 20 begins to escape and the vapor pressure in the second chamber 20 begins to decrease. The rate of the decrease in vapor pressure in the second chamber 20 will depend on the size of the vent hole 642, the thermodynamics of the system (the temperature and pressure of the propellant in particular, and the speed at which the vent hole is opened (i.e. change from fully closed to fully open).

Figure 1D:
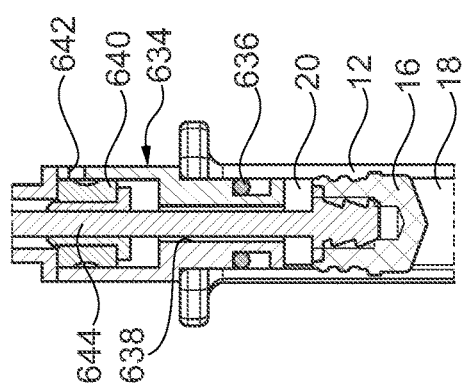
FIG. 1D shows the syringe of FIGS. 1A and 1B with the vent hole fully open.
Figure 1C:
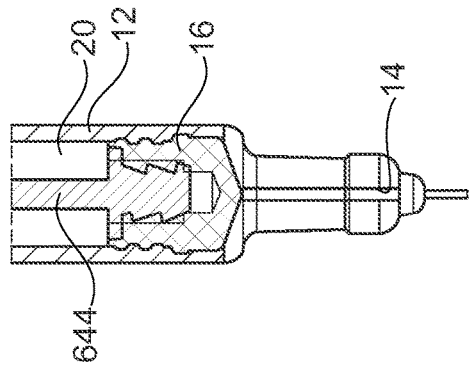
FIG. 1C shows the axial position of the stopper that corresponds to the configuration shown in FIG. 1B.

FIG. 1C shows the axial position of the stopper 16 corresponding to the configuration shown in FIG. 1B. As can be seen in FIG. 1C, the stopper 16 is not at its axially forwardmost position within the barrel 12, and the first volume 18 still contains medicament.

In the embodiment shown in FIGS. 1A to 1E, the vent hole 642 is sized so that when the vent hole 642 is first opened, a sufficient amount of propellant remains for a long enough time in the second chamber 20 to move the stopper 16 to its forwardmost position in the syringe barrel 12.

Figure 1E:
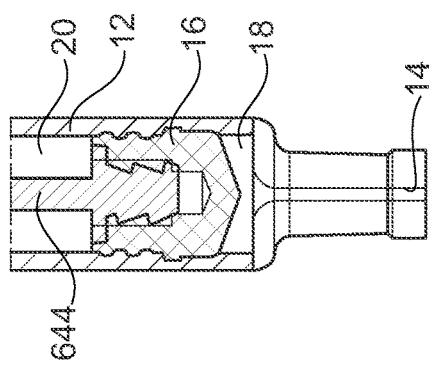
FIG. 1E shows the axial position of the stopper that corresponds to the configuration shown in FIG. 1D.

FIG. 1D shows the axially moveable seal 640 in an axial position that is entirely forward of the vent hole 642 such that the vent hole is fully open. FIG. 1E shows the axial position of the stopper 16 corresponding to the configuration shown in FIG. 1D.

Figure 2:
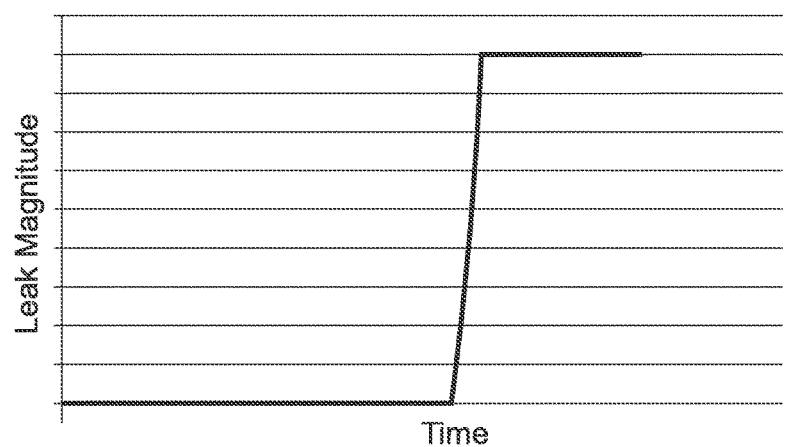
FIG. 2 shows a plot of leak magnitude versus time for the syringe shown in FIGS. 1A to 1E.

FIG. 2 shows the leak magnitude of the embodiment of FIGS. 1A to 1E as the axially moveable seal 640 moves axially and opens the vent hole 642.

FIGS. 3A and 3B show examples corresponding to the embodiment of FIGS. 1A to 1E. In FIG. 3A, the propellant housing has an inlet 634a at a rear end, where the inlet 634a is fluidly connected to a propellant source 628. In use the propellant source 628 provides liquid propellant to the second chamber 20, which, in the embodiment of FIG. 3A, is the volume between the propellant source 628 and the stopper 16. In FIG. 3B, the rear end of the propellant housing 634 is sealed and, instead, the propellant housing 634 has a side inlet 634a. In any embodiment, there must be a fluidic flow path from the propellant source 628 that permits the vapor pressure in the second chamber 20 to act on and cause the stopper 16 to move.

Figure 4A:
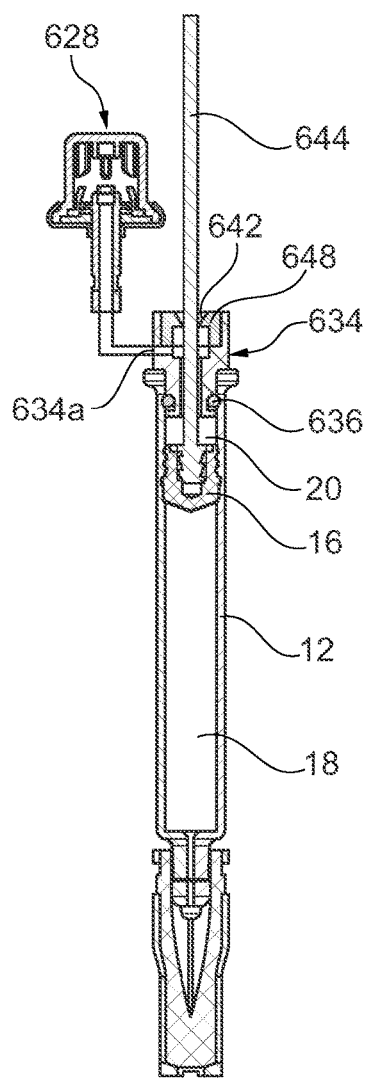
FIGS. 4A and 4B show a syringe in accordance with an alternative embodiment of the present invention that includes a vent hole, where in FIG. 4A the vent hole is closed, and in FIG. 4B the vent hole is open.
Figure 4B:
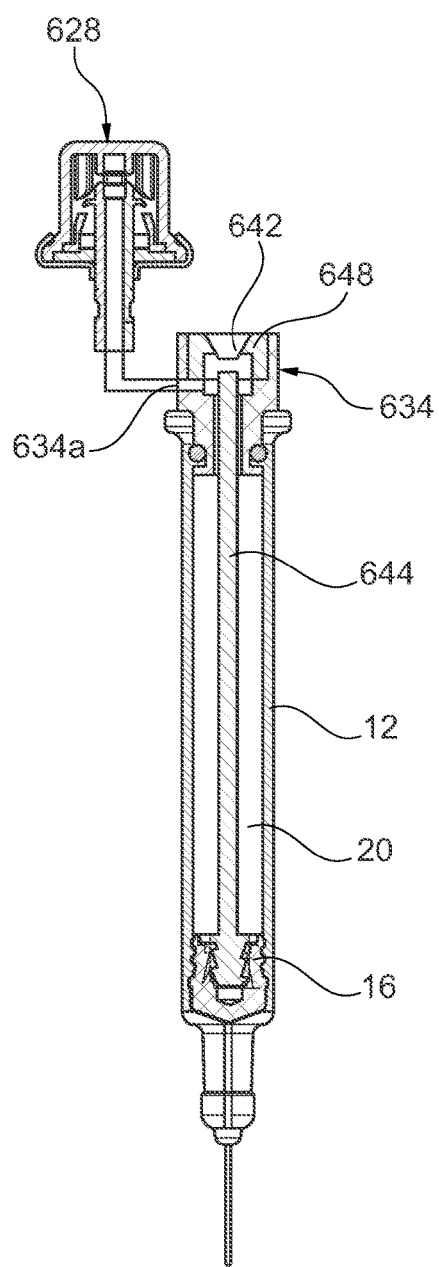

In the alternative embodiment shown in FIGS. 4A and 4B, the propellant housing 634 has a vent hole 642 located at a rear end such that the rod 644 initially protrudes therethrough. FIG. 4A shows the device in an initial configuration prior to delivery of medicament. In this initial configuration, a rod seal 648 seals the propellant housing 634 to the rod 644 so as to block the vent hole 642.

In use, a propellant source 628 dispenses liquid propellant through an inlet 634a of the propellant housing 634 into the second chamber 20 where it may boil and cause the stopper 16 to move axially forwardly. The advancing stopper 16 causes the rod 644 to slide axially forwardly through the rod seal 648. Throughout this movement, the combination of the rod seal 648 and the rod 644 continues to seal the vent hole.

When the stopper 16 reaches its axially forwardmost position in the syringe barrel 12, as shown in FIG. 4B, the rear end of the rod 644 will have moved to an axial position where the vent hole 642 is no longer sealed by the combination of the rod seal 648 and the rod 644, and venting of propellant from the second chamber 20 begins. The movement of the rod 644 may cause the vent hole 642 to be opened entirely, or it may create a restricted flow path.

Figure 5:
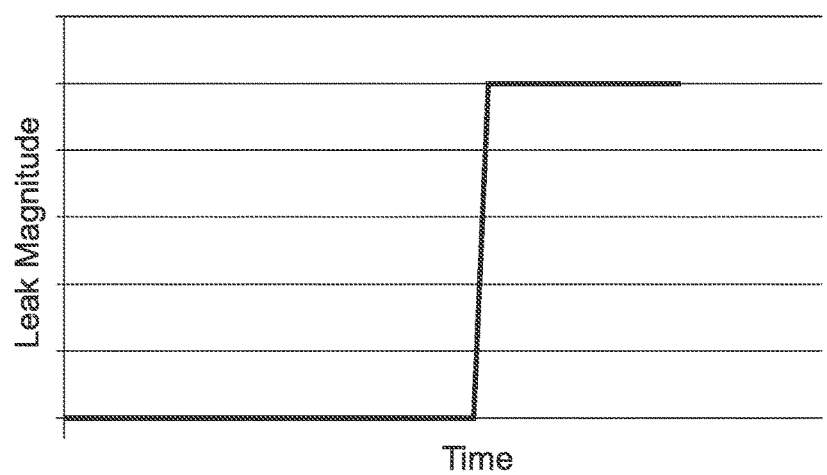
FIG. 5 shows a plot of leak magnitude versus time for the syringe shown in FIGS. 4A and 4B.

FIG. 5 shows the leak magnitude of the embodiment of FIGS. 4A and 4B as the rod 644 moves axially to open the vent hole 642. In the embodiment of FIGS. 4A and 4B, the size of the vent hole 642 is determined by the diameter of the rod 644 and is therefore larger than the smaller vent hole 642 of the embodiment of FIGS. 1A to 1E, 3A and 3B. Consequently, the leak magnitude shown in FIG. 5 increases more rapidly than the leak magnitude shown in FIG. 2.

As described above, a further alternative embodiment is shown in FIGS. 6A and 6B in which vapor pressure acting on the rod 644 (and piston seal 650) causes axial movement of the stopper 16 so as to expel medicament from the first chamber 18. In this sense, the second chamber 20 is defined as the volume extending between a propellant source 628 and the rear end of the rod 644 (which forms part of the stopper 16) that is sealed against the syringe barrel 12. The propellant housing 634 has an inlet 634a in fluid communication with the propellant housing 628 and further includes a vent hole 642 that is positioned so as to be in fluid communication with the second chamber 20 when the stopper 16 is in its forwardmost axial position in the syringe barrel 12 (i.e. at the end of delivery) as shown in FIG. 2B, or, in alternative embodiments, when the stopper 16 is approaching its forwardmost axial position.

In the configuration shown in FIG. 6A prior to medicament delivery, the vent hole 642 is not in fluid communication with the second chamber 20 and so propellant is not able to vent and, instead, causes axial movement of the stopper 16 (including rod 644). At the end of delivery, as shown in FIG. 6B, the rod 644 and piston seal 650 have moved axially forwardly sufficiently for the vent hole 642 to open and permit venting of propellant from the second chamber 20.

Figure 6C:
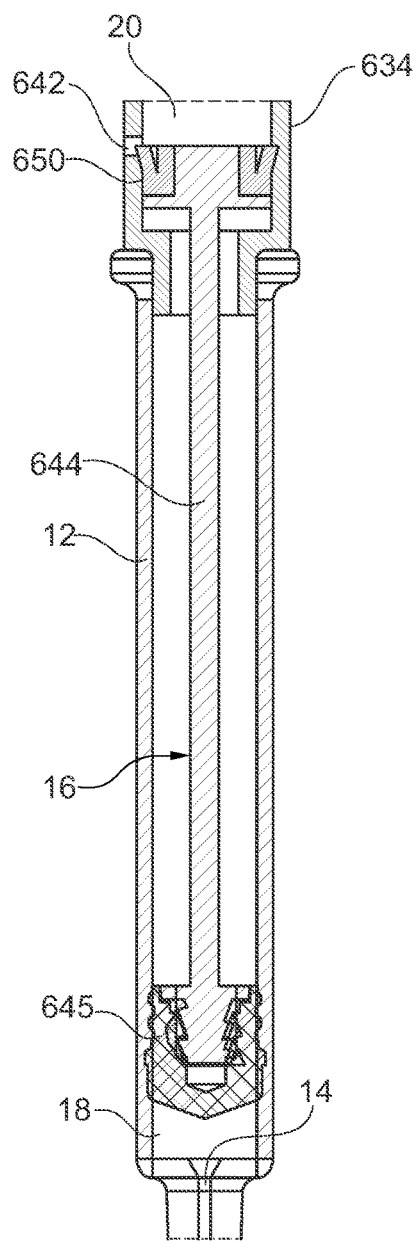
FIGS. 6C and 6D show a syringe in accordance with an alternative embodiment of the present invention, wherein in FIG. 6C the vent hole is partially open, and in FIG. 6D the vent hole is entirely open.
Figure 6D:
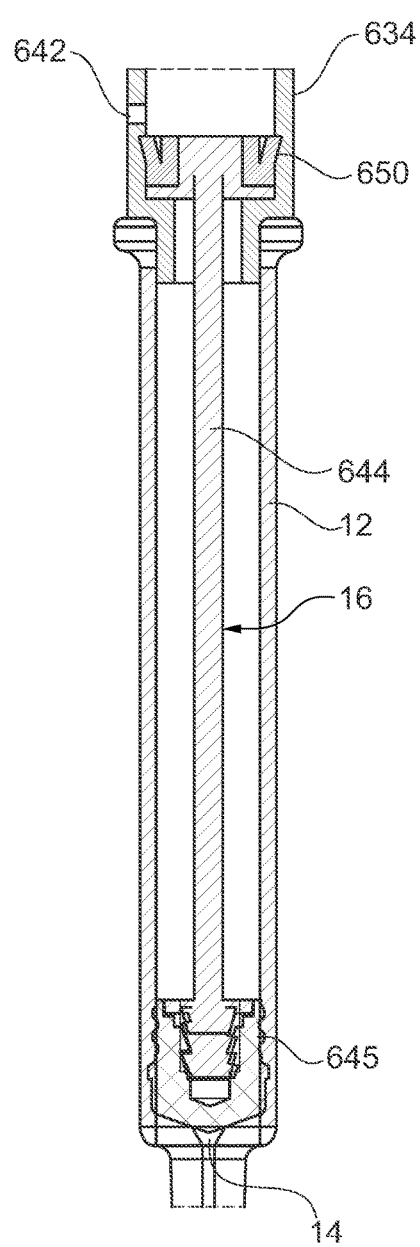

FIGS. 6C and 6D show a variation of the embodiment of FIGS. 6A and 6B according to an alternative embodiment of the present invention. FIG. 6C shows a configuration in which the vent hole 642 has just opened and the stopper 16 is not in its forwardmost axial position. FIG. 6D shows a configuration in which the vent hole 642 is fully open and the stopper 16 is in its forwardmost axial position. In order to ensure that the stopper 16 does not immediately stop moving axially forwardly as soon as the vent hole 642 opens, it is preferable for there to be liquid propellant remaining in the syringe which may vaporize to provide sufficient vapor pressure in the (now vented) second chamber 20 to continue moving the stopper 16. Indeed, to ensure that the stopper 16 reaches its forwardmost axial position in the barrel 12 it is preferable for there initially to be enough liquid propellant in the syringe such that some liquid propellant remains in the syringe when the stopper 16 reaches its forwardmost axial position in the barrel 12 despite the vent hole 642 opening in the meantime.

In some preferable embodiments (not limited to that described above in relation to FIGS. 6C and 6D), the vent hole has an axial length and the axial distance between the stopper when the vent hole first opens and the stopper in its final axial position (which is preferably at the forwardmost axial possible position in the barrel) is greater than the axial length of the vent hole. This axial distance may be at least two times greater than the axial length of the vent hole. In some embodiments, this axial distance may be greater than 1 mm. In alternative embodiments, this axial distance may be less than 1 mm. In a 1 ml long syringe, an axial distance of 1 mm corresponds to approximately 0.03 cc volume.

Figure 7:
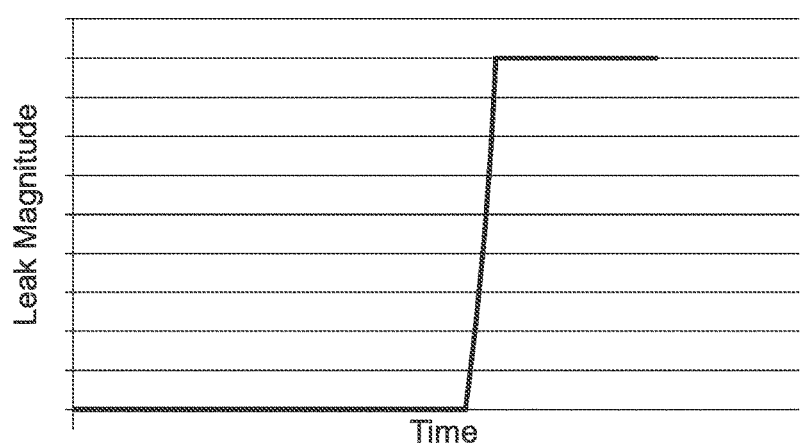
FIG. 7 shows a plot of leak magnitude versus time for the syringe shown in FIGS. 6A and 6B.

FIG. 7 shows the leak magnitude of the embodiment of FIGS. 6A and 6B (or the embodiment of FIGS. 6C and 6D) as the rod 644 moves axially to open the vent hole 642. As with the embodiment of FIGS. 1A to 1E, the vent hole 642 may be sufficiently small so as to restrict venting and permit medicament delivery to continue for a time period following initial venting.

Contrasting the embodiment of FIGS. 6A and 6B to that of FIGS. 1A to 1E, the embodiment of FIGS. 6A and 6B will encounter higher frictional forces during medicament delivery due to the presence of the piston seal 650. However, since the vapor pressure acts on the rod 644 and the piston seal 650 which are not limited by the diameter of the syringe barrel 12, a larger surface area is permissible which allow greater delivery forces to be employed.

The alternative embodiment shown in FIGS. 8A to 8C is very similar to that shown in FIGS. 1A to 1E but for the fact that the stopper 16 is connected to the axially moveable seal 640 by an extendible member 644' rather than a rigid rod. As the stopper 16 moves axially forwardly in the syringe barrel 12, the extendible member 644' extends. As the stopper 16 approaches its axially forwardmost position in the syringe barrel 12, the extendible member 644' extends to its fullest extent and, due to tension, begins to cause axially forward movement of the axially moveable seal 640. Consequently, the axially moveable seal 640 moves to an axial position where the vent hole 642 is opened and permits venting of propellant from the second chamber 20.

FIG. 8C shows a detailed view of an example of a suitable extendible member 644' that is in a coiled configuration. Axial movement of the stopper 16 causes the coil to unwind. Once the coil has fully unwound, the extendible member 644' may apply a downward axial force on the axially moveable seal 640 to open the vent hole 642. The extendible member 644' may be any suitable member that is flexible so as to only apply a force to the axially moveable seal 640 sufficient to move the axially moveable seal 640 when the distance between the stopper 16 and the axially moveable seal 640 substantially equals the maximum length of extendible member 644'. A length of string or similar member may be a suitable extendible member 644'.

Figure 8D:
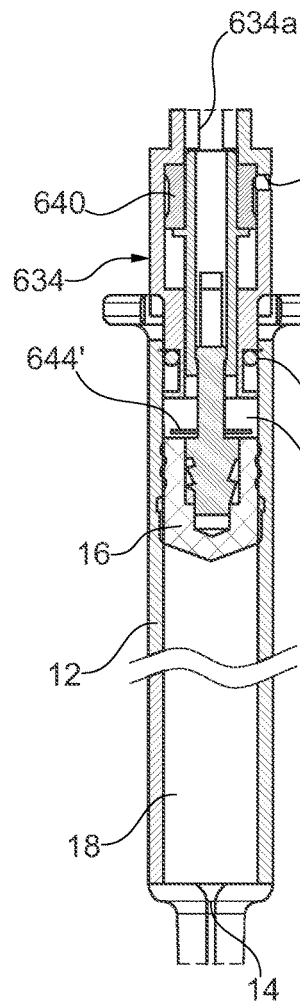
FIGS. 8D to 8F show a syringe in accordance with an alternative embodiment of the present invention that, where in FIG. 8D the vent hole is closed, in FIG. 8E the vent hole is open and the stopper is not in its forwardmost position in the barrel, and in FIG. 8F the vent hole is open and the stopper is in its forwardmost position in the barrel.
Figure 8E:
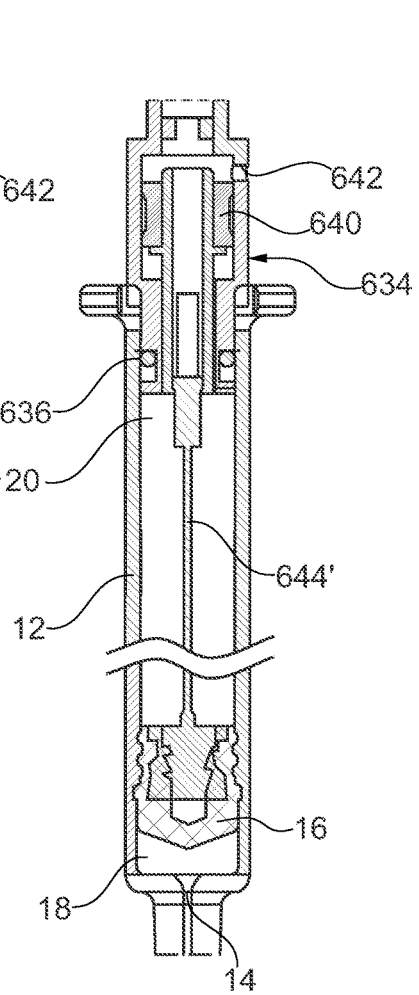
Figure 8F:
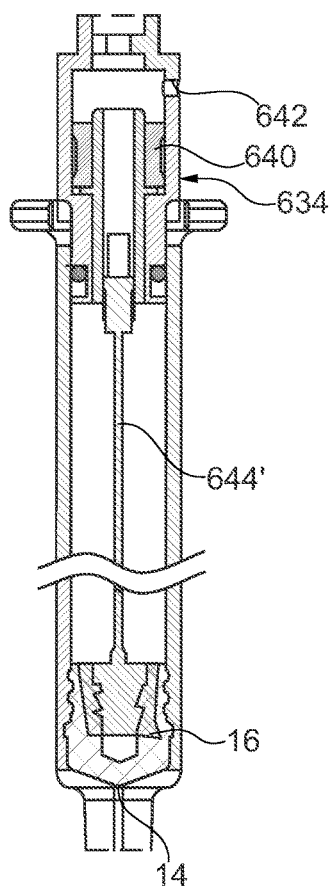

FIGS. 8D to 8F show a variation of the embodiment of FIGS. 8A to 8C within the scope of the present invention. FIG. 8D shows a configuration in which the vent hole 642 is blocked by the axially moveable seal 640. FIG. 8E shows a configuration in which the vent hole 642 is open (i.e. is not fully blocked by the axially moveable seal 640) and the stopper 16 is not in its forwardmost axial position in the barrel 12. FIG. 8F shows a configuration in which the vent hole 642 is fully open and the stopper 16 is in its forwardmost axial position in the barrel 12. As described above in relation to FIGS. 6C and 6D, it is preferable for there to be liquid propellant remaining in the syringe which may vaporize to provide sufficient vapor pressure in the (now vented) second chamber 20 to continue moving the stopper 16. Indeed, to ensure that the stopper 16 reaches its forwardmost axial position in the barrel 12 it is preferable for there initially to be enough liquid propellant in the syringe such that some liquid propellant remains in the syringe when the stopper 16 reaches its forwardmost axial position in the barrel 12 despite the vent hole 642 opening in the meantime. Such an arrangement is not limited to the embodiment of FIGS. 6C and 6D or of FIGS. 8D to 8F, but may be applicable to any embodiment within the scope of the present invention in which the vent hole opens when the stopper 16 is not at its forwardmost axial position in the barrel 12.

Figure 9:
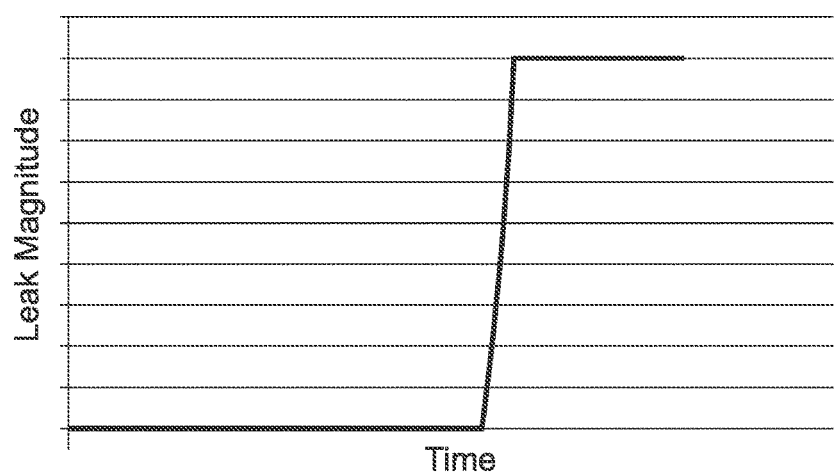
FIG. 9 shows a plot of leak magnitude versus time for the syringe shown in FIGS. 8A and 8B.

FIG. 9 shows the leak magnitude of the embodiment of FIGS. 8A to 8C (or the embodiment of FIGS. 8D to 8F) as the axially moveable seal 640 moves axially and opens the vent hole 642. The leak magnitude shown in FIG. 9 closely resembles that shown in FIG. 2 due to the similarities in the embodiments of FIGS. 1A to 1E and FIGS. 8A to 8C.

Figure 10A:
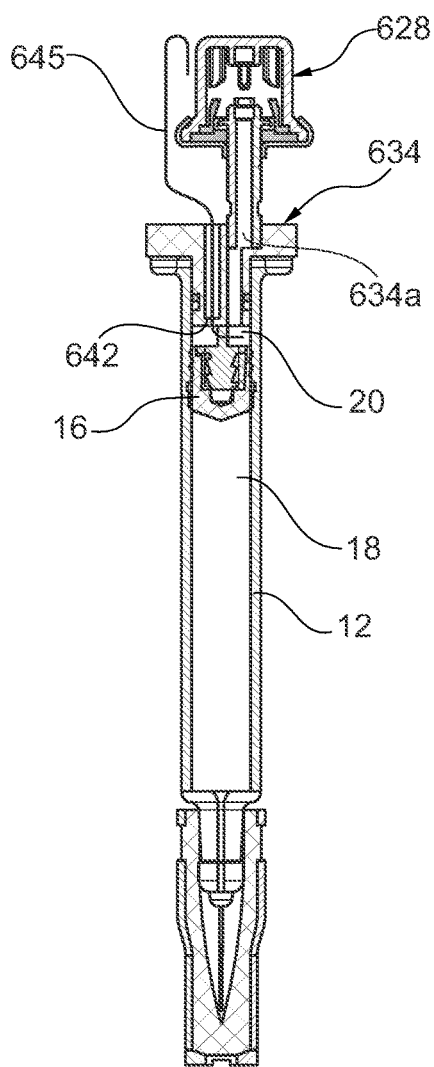
FIGS. 10A and 10B show a syringe in accordance with an alternative embodiment of the present invention that includes a vent hole, where in FIG. 10A the vent hole is occluded, and in FIG. 10B the vent hole is not occluded and is open.
Figure 10B:
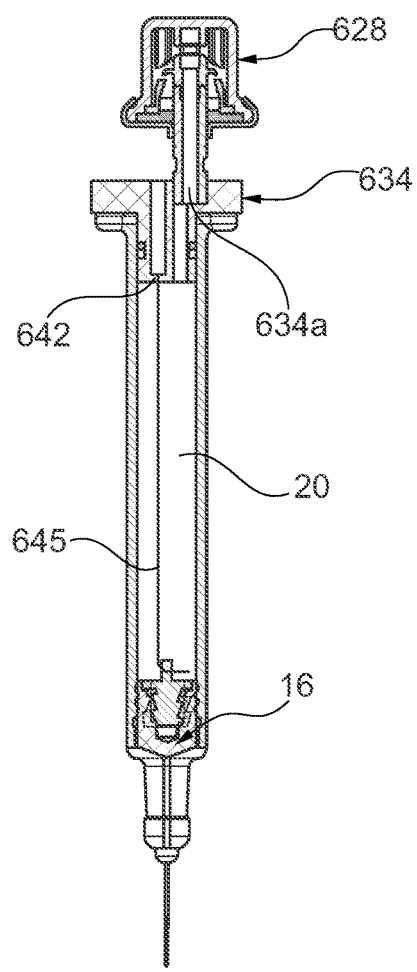

A further alternative embodiment is shown in FIGS. 10A and 10B. In this embodiment, the propellant housing 634 has a vent hole 642 that is open, to a certain extent, prior to propellant being released into the second chamber 20. A flexible member 645 extends axially rearwardly from the stopper 16 and extends through the vent hole 642. The presence of the flexible member 645 in the vent hole 642 does not prohibit propellant venting from the second chamber 20 therethough, however it does limit the rate at which propellant may vent. The absolute size of the vent hole 642 and the relative size of the vent hole 642 relative to the dimensions of the flexible member 645 will determine the rate at which propellant may vent from the second chamber 20. Clearly, it is preferable for the leak rate to be low enough for the propellant remaining to deliver a full dose of medicament.

At the end of medicament delivery when the stopper 16 is at its axially forwardmost position in the syringe barrel 12 as shown in FIG. 10B, the flexible member 645 no longer occludes the vent hole 642 and so permits more rapid venting of any propellant remaining in the second chamber 20. In alternative embodiments, the flexible member 645 may remain in an occluding position when the stopper 16 is in its axially forwardmost position.

Figure 11:
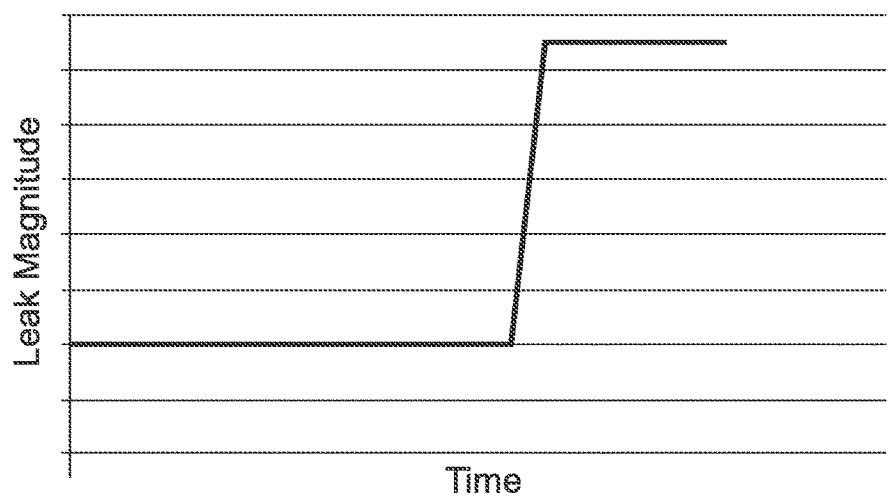
FIG. 11 shows a plot of leak magnitude versus time for the syringe shown in FIGS. 10A and 10B.

FIG. 11 shows the leak magnitude of the embodiment of FIGS. 10A and 10B as propellant vents from the second chamber 20 via the occluded vent hole 642.

Figure 12A:
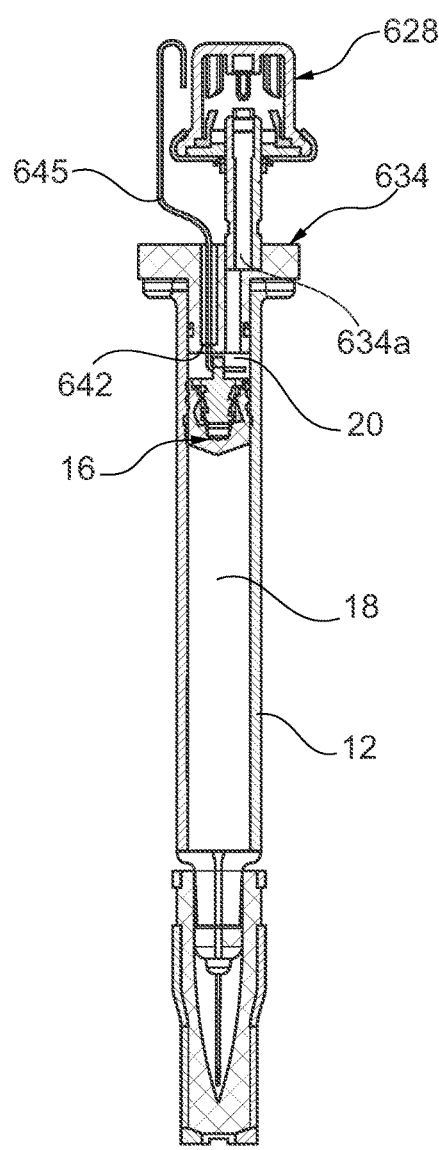
FIGS. 12A and 12B show a syringe in accordance with an alternative embodiment of the present invention that includes a vent hole, where in FIG. 12A the vent hole is occluded, and in FIG. 12B the vent hole is still occluded and the stopper is at its forwardmost axial position in the syringe barrel.

FIGS. 12A and 312B show an embodiment related to that shown in FIGS. 10A and 10B. The embodiment of FIGS. 12A and 12B differs from that shown in FIGS. 10A and 10B in that the vent hole 642 extends axially to a greater extent in the embodiment of FIGS. 12A and 12B. The presence of flexible member 645 in the vent hole 642 therefore provides an occlusion over a greater length and consequently limits venting therethrough to a greater extent compared to the embodiment of FIGS. 10A and 10B.

Figure 13:
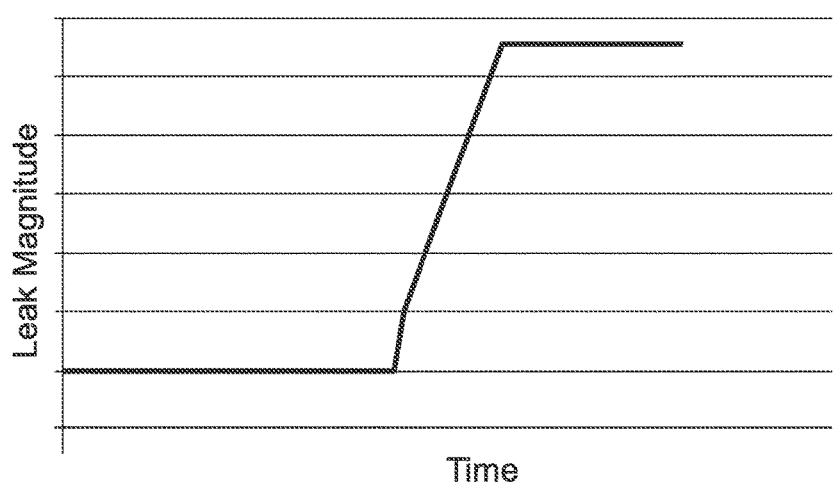
FIG. 13 shows a plot of leak magnitude versus time for the syringe shown in FIGS. 12A and 12B.

This slower leak rate is evident in FIG. 13 where it can be seen that the leak magnitude increases more slowly compared with FIG. 11.

Figure 12B:
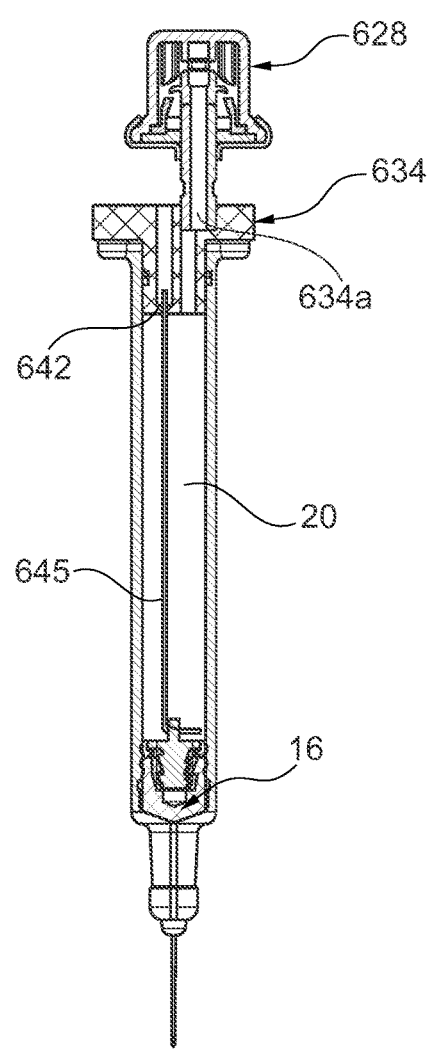
Figure 12C:
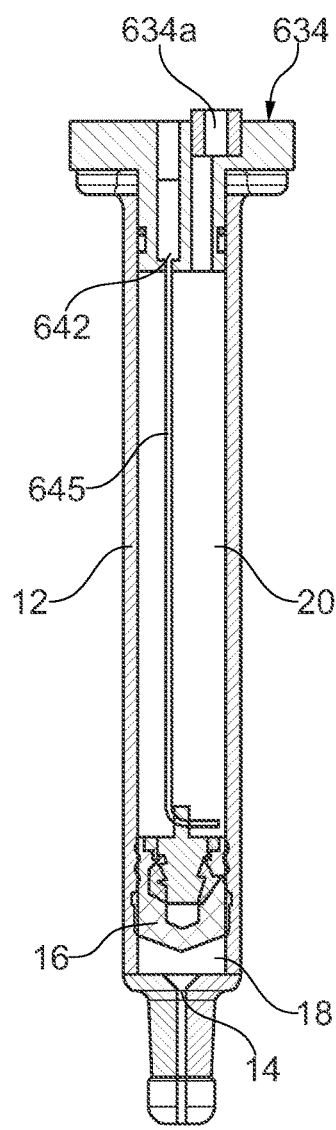
FIGS. 12C and 12D show a syringe in accordance with an alternative embodiment of the present invention that includes a vent hole, where in FIG. 12C the vent hole is not occluded and the stopper is not in its forwardmost position in the barrel, and in FIG. 12D the vent hole is not occluded and the stopper is in its forwardmost position in the barrel.
Figure 12D:
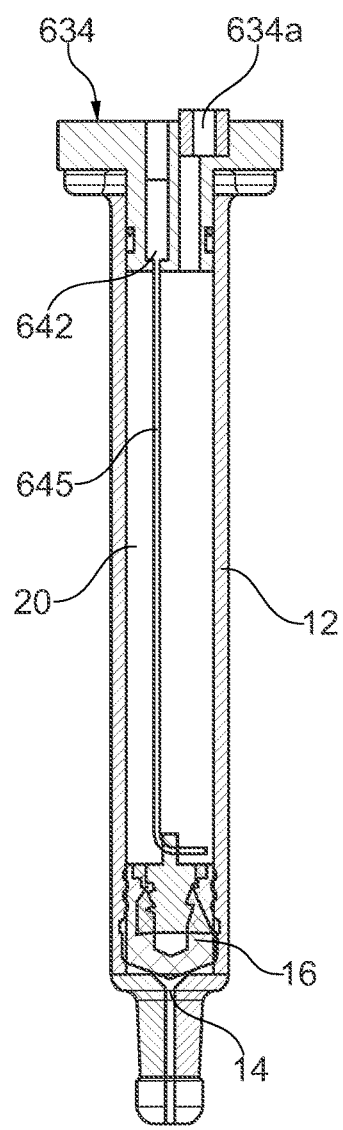

FIGS. 12C and 12D show a variation of the embodiment of FIGS. 12A and 12B within the scope of the present invention. FIG. 12C shows a configuration in which the flexible member 645 has just been fully withdrawn from the vent hole 642 thereby fully opening the vent hole 642. In the configuration shown in FIG. 12C, the stopper 16 is not in its forwardmost axial position in the barrel 12. FIG. 12D shows a configuration in which the vent hole 642 is fully open and the stopper 16 is in its forwardmost axial position in the barrel 12. It is preferable for there the be liquid propellant present in the syringe when the configuration shown in FIG. 12C is reached so that sufficient vapor pressure may be provided to the second chamber 20, despite the venting, to cause the stopper 16 to move to its forwardmost axial position in the barrel 12 as shown in FIG. 12D. It is further preferable to initially provide sufficient liquid propellant such that some still remains in the syringe when the stopper 16 reaches its forwardmost axial position in the barrel 12.

A further alternative embodiment is shown in FIGS. 14A and 14B which is similar to that described above in relation to FIGS. 4A and 4B. The embodiment of FIGS. 14A and 14B differs from that of FIGS. 4A and 4B in that the rod 644 of FIGS. 14A and 14B is flexible so as to permit a reduction in the overall axial length of the device prior to actuation. As shown in FIG. 14A, the part of the flexible rod 644 that is initially disposed outside of the syringe barrel 12 may bend so as remain compact and permit a more compact device. As the stopper 16 moves axially forwardly, the flexible rod 644 is drawn through the rod seal 648 and eventually moves to a position where it no longer prevents venting of propellant through the vent hole 642 as shown in FIG. 14B. The rod 644 may be hollow to permit flexing.

Throughout the present specification, the term "syringe" relates to and includes any medicament delivery device having a medicament container with an outlet and a moveable stopper for expelling medicament therefrom. As examples, the syringe may include a needle, a nozzle or a conduit attached to the outlet. In other embodiments, the syringe may not include any further components downstream of the outlet. The syringe of the present invention may be or form part of a subcutaneous delivery device, a nasal delivery device, an otic delivery device, an oral delivery device, an ocular delivery device, an infusion device or any other suitable medicament delivery device.

Directions described herein as "axial" correspond to directions parallel to the longitudinal length of the syringe.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A syringe propellable by a propellant that boils at a predetermined temperature, the syringe comprising:
   a barrel having an outlet at a front end;
   a needle in fluid communication with the outlet;
   a stopper axially moveable in the barrel; and a third chamber containing propellant;
   wherein the stopper defines and separates a first chamber and a second chamber, the first chamber being axially forwards of the stopper and being configured for containing a medicament, and the second chamber being axially rearwards of the stopper and being configured to receive propellant for acting on the stopper to move the stopper axially forwardly in the barrel to expel medicament through the outlet upon actuation of the syringe;
   the syringe further comprising a vent hole arranged to permit propellant to vent out of the second chamber through the vent hole;
   the syringe being configured such that, in use, upon actuation of the syringe, liquid propellant is released from the third chamber and boils outside of the third chamber at or above the predetermined temperature to provide an increasing vapor pressure in the second chamber that causes the stopper to move axially forwardly and begin to expel medicament from the first chamber through the outlet;
   wherein during forward axial movement of the stopper in the barrel, propellant vents away from the second chamber through the vent hole so that the syringe is automatically depressurized over a time period following actuation of the syringe; wherein the stopper is axially moveable in the barrel between:
   a first position in which the vent hole is not in fluid communication with the first chamber or the second chamber;
   a second position axially forward of the first position in which the vent hole is in fluid communication with the second chamber thereby permitting venting of propellant from the second chamber; and
   a third position that is axially forward of the second position, said third position being the forwardmost possible position of the stopper in the barrel in which the first chamber has substantially zero volume and substantially all medicament has been expelled from the first chamber;
   wherein the third chamber initially contains a sufficient volume of liquid propellant such that the syringe contains liquid propellant when the stopper reaches the third position.

2. The syringe according to claim 1, wherein in said first position the stopper blocks fluid communication between the vent hole and the first chamber and between the vent hole and the second chamber, and in said second position the stopper is axially forward of at least part of the vent hole such that the vent hole is in fluid communication with the second chamber.

3. The syringe according to claim 2, wherein said stopper comprises a bung and a piston extending axially rearwardly from said bung, wherein each of said bung and said piston seals to the barrel, said piston being configured to be acted upon by vapor pressure in the second chamber so as to cause said stopper to move axially in the barrel.

4. The syringe according to claim 1, further comprising a blocking member that is moveable between a blocking position in which fluid communication between the vent hole and the second chamber is blocked by the blocking member, and a non-blocking position in which the vent hole is in fluid communication with the second chamber;
   wherein the blocking member is moveable between the blocking position and the non-blocking position by the stopper such that in the first position the blocking member is in the blocking position and in the second position the blocking member is in the non-blocking position.

5. The syringe according to claim 1, wherein said propellant includes a hydrofluoroalkane (HFA).

6. A syringe according to claim 5, wherein said HFA is HFA 134a.

7. The syringe according to claim 1, wherein the vent hole has an axial length and the axial distance between the stopper in the second position and the stopper in the third position is greater than the axial length of the vent hole.

* * * * *